Figure 1:
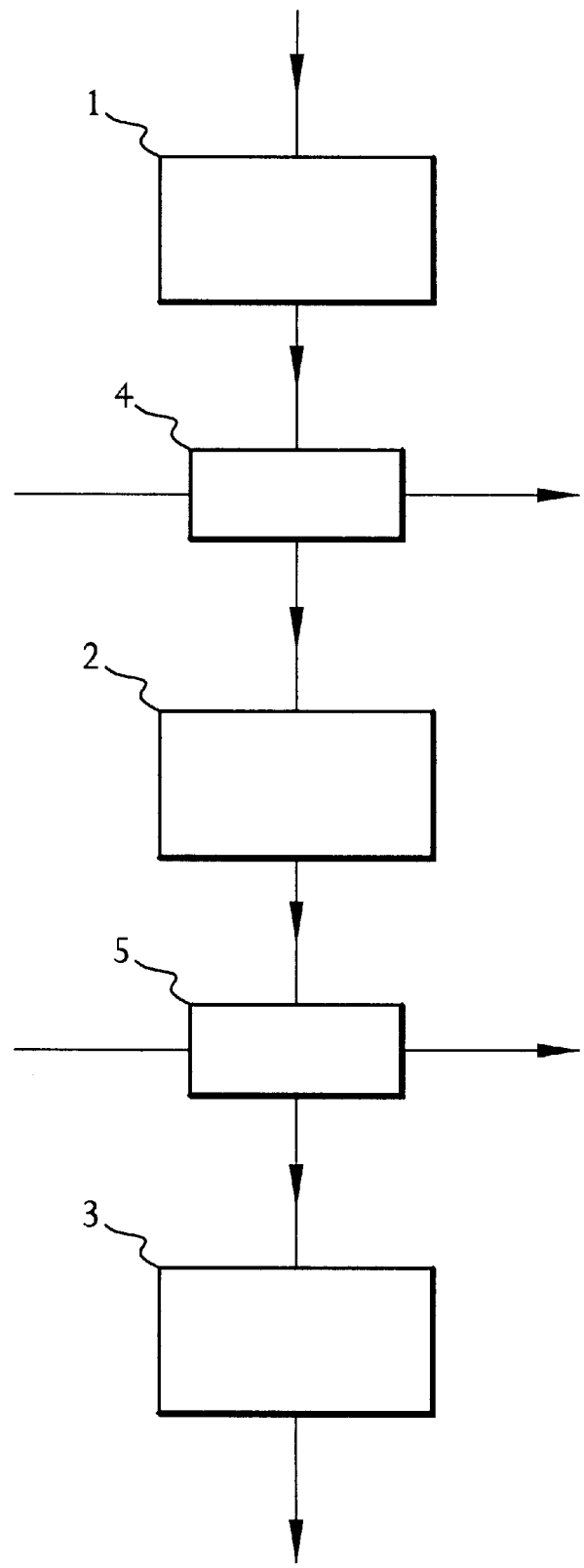

United States Patent

Crewdson et al.

[11] Patent Number: 6,011,188
[45] Date of Patent: Jan. 4, 2000

[54] MULTI-BED SELECTIVE HYDROGENATION OF ACETYLENES

[75] Inventors: Bernard John Crewdson, North Yorkshire; Fredrick Ernest Hancock, Cleveland, both of United Kingdom

[73] Assignee: Imperial Chemical Industries PLC, United Kingdom

[21] Appl. No.: 08/637,817

[22] PCT Filed: Nov. 14, 1994

[86] PCT No.: PCT/GB94/02501

§ 371 Date: May 3, 1996

§ 102(e) Date: May 3, 1996

[87] PCT Pub. No.: WO95/15365

PCT Pub. Date: Jun. 8, 1995

[30] Foreign Application Priority Data

Dec. 1, 1995 [GB] United Kingdom ................ 9324685

[51] Int. Cl.$^7$ ................ C07C 5/08; C07C 5/09
[52] U.S. Cl. ................ 585/259; 585/263; 585/265
[58] Field of Search ................ 585/259, 263, 585/265, 952; 561/881

[56] References Cited

U.S. PATENT DOCUMENTS

| | | |
|---|---|---|
| 3,412,169 | 11/1968 | Clark . |
| 3,471,582 | 10/1969 | Lupfer . |
| 3,656,911 | 4/1972 | Hobbs . |
| 4,236,219 | 11/1980 | Killebrew, Jr. et al. ............ 364/501 |
| 4,249,908 | 2/1981 | Funk . |
| 5,254,758 | 10/1993 | Hiles et al. ............ 568/881 |

FOREIGN PATENT DOCUMENTS 0 029 321  5/1981  European Pat. Off. .

*Primary Examiner*—Wayne Langel

[57] ABSTRACT

Compensation for catalyst activity decline in multi-bed selective hydrogenation of acetylenes in the presence of olefins by providing inter-bed heating so that the product from the first bed is heated before it is fed to the second bed, and the temperature at which the product from the first bed is fed to the second bed is increased as the catalyst activity declines. In a modification, when the catalyst is fresh, the product from the first bed is cooled before it is fed to the second bed, but, as the catalyst activity declines the temperature at which the product from the first bed is fed to the second bed is increased, so that after a period of use the product from the first bed is heated before it is fed to the second bed.

6 Claims, 1 Drawing Sheet

MULTI-BED SELECTIVE HYDROGENATION OF ACETYLENES

This invention relates to hydrogenation and in particular to the selective catalytic hydrogenation of acetylene in the presence of olefins.

Olefins are often produced by reforming or cracking a hydrocarbon feedstock such as naphtha: as a result of the production process, small proportions of acetylene and other more highly unsaturated compounds are often formed. It is normally desirable to remove the acetylene before further processing of the olefin product.

While it is often possible to effect partial separation by fractionation, removal of the acetylene to very low levels by fractionation is often difficult. Consequently it is more usual to selectively hydrogenate the acetylene in the presence of the olefins, for example using a supported palladium catalyst as described in U.S. Pat. No. 4,329,530.

Since the hydrogenation reaction is exothermic, and low hydrogenation temperatures are required in order to minimise the hydrogenation of the olefins present, the selective hydrogenation is normally effected using a series of adiabatic catalyst beds with inter-bed cooling. Alternatively an isothermal bed, followed by one or more adiabatic beds, is sometimes employed with the temperature in the isothermal bed maintained essentially constant by means of suitable heat exchange means within the bed to extract the heat of reaction into a suitable coolant: again it is normal to operate the beds at successively decreasing bed temperatures, and so inter-bed cooling is required.

A series of beds, rather than a single bed, is normally used to keep the temperature to a minimum since as the temperature increases, the hydrogenation becomes less selective and an increasing amount of the olefins become hydrogenated. Furthermore as the temperature increases, there is a risk of run-away reactions occurring. Thus in operation, part of the desired hydrogenation is effected in a first catalyst bed, without an undue temperature rise, and then the product from the first bed is cooled and passed through a second catalyst bed in order to effect further hydrogenation. Further catalyst beds, with inter-bed cooling, may be employed: the number of beds used will normally depend on the acetylene and content of the feed and the desired acetylene content of the product. Typically there may be a total of 2 to 5 beds. Using typical selective hydrogenation catalysts such as a support impregnated with small amounts, eg 0.02 to 0.5% by weight, of palladium, the catalyst bed inlet temperature is generally in the range 50–100° C., particularly 50–90° C. As is well known, it is generally desirable to have a small proportion of carbon monoxide, eg 200–1500 ppm by volume, in the gas stream subjected to selective hydrogenation.

The hydrogenation catalyst generally gradually loses activity over a period of use: often this loss of activity is a result of poisoning of the catalyst with impurities, particularly sulphur, iron, and/or arsenic compounds, in the feed and by formation of organic compounds, such as polymers, which accumulate on the surface of the catalyst. Consequently, as the catalyst activity decreases it is the normal practice to increase the temperature at which the feed is fed to the first bed. For example during the normal life of the catalyst the inlet temperature may gradually be increased from an initial value of about 60° C. to an "end-of-life" inlet temperature of about 90° C. One consequence of this is that, as the activity of the catalyst decreases and the inlet temperature is increased to compensate for the loss of activity, the proportion of olefins hydrogenated gradually increases.

We have devised a method whereby the increasing effective loss of olefins resulting from such increased unwanted hydrogenation as the catalyst activity declines may be minimised.

In the present invention, in order to compensate for the decline of catalyst activity, instead of increasing the temperature at which the mixture is fed to the first bed and providing cooling so that the product from the first bed is cooled before it enters the second bed the feed temperature to the first bed is maintained at such a level that the first bed exit temperature is below the temperature at which it is necessary to feed the product from the first bed to the second bed in order to reduce the concentration of acetylene to said specified level and the product from the first bed is heated before entry into the second bed.

Accordingly the present invention provides a process for the selective hydrogenation of acetylene in the presence of olefins to decrease the concentration of acetylene to below a specified level, wherein a hydrocarbon feedstock containing olefins and acetylene together with hydrogen, is passed through a series of beds containing a selective hydrogenation catalyst whose activity declines over a period of use with the product from the first bed being heated before it is fed to the second bed and in order to achieve a reduction of the concentration of acetylene to below said specified level the temperature at which the product from the first bed is fed to the second bed is increased as the activity of the catalyst declines.

The invention is illustrated by reference to the accompanying drawing which represents a typical flowsheet employing three beds.

Referring to the figure, a series of three adiabatic beds 1, 2, 3 are shown with heat exchangers 4, 5 in the lines connecting the beds 1 and 2 and beds 2 and 3 respectively. The feed gas eg a mixture of hydrogen, methane, ethene, ethane, and ethyne (acetylene), and possibly higher hydrocarbons, is fed to the first bed 1 at a first bed inlet temperature. Hydrogenation takes place reducing the acetylene concentration. As a result of the hydrogenation taking place in bed 1. the temperature increases. In addition to hydrogenation of the acetylene to ethene, some hydrogenation of ethene to ethane takes place.

In conventional operation, the product from bed 1 is cooled in heat exchanger 4 to the desired inlet temperature for bed 2. Further hydrogenation takes place in bed 2 giving a further decrease in acetylene concentration again giving rise to a temperature increase. Similarly the product from bed 2 is cooled in heat exchanger 5 to the desired inlet temperature for bed 3 and further hydrogenation takes place in bed 3, again with a temperature rise to give a product having the desired acetylene content. As in bed 1, some hydrogenation of ethene takes place in beds 2 and 3.

As the catalyst activity declines, eg as a result of gradual poisoning of the catalyst, in conventional operation it is necessary to increase the bed inlet temperatures in order that the acetylene content of the product is decreased to the desired level. This temperature increase inevitably gives rise to increased hydrogenation of the olefins present.

In the present invention, instead of increasing the inlet temperature of bed 1 as the activity declines, the feed temperature thereto is kept low. As a result the amount of acetylene hydrogenation occurring in the first bed decreases substantially as the catalyst activity declines and so the heat generated in the first bed decreases, giving a much smaller temperature increase and hence a lower temperature at which the product leaves the first bed. As a consequence, in order to achieve the desired product from bed 3, more hydrogenation has to be effected in beds 2 and 3, necessitating increased feed temperatures thereto. In view of the reduced temperature rise in bed 1, the bed 1 exit temperature is below the required inlet temperature for bed 2 and so, instead of cooling the product from bed 1 in heat exchanger 4, it is necessary to heat that product to the desired bed 2 inlet temperature.

In a modification of the process inter-bed cooling between the first and second beds may be provided when the catalyst is fresh, ie has high activity, but, when the catalyst activity declines, the conditions are modified so that the product from the first bed is heated before it enters the second bed.

Accordingly a modification of the invention provides a process for the selective hydrogenation of acetylene in the presence of olefins to decrease the concentration of acetylene to below a specified level, wherein a hydrocarbon feedstock containing olefins and acetylene, together with hydrogen, is passed through a series of beds containing a selective hydrogenation catalyst whose activity declines over a period of use, with the product from the first bed being cooled before it is fed to the second bed when the catalyst is fresh, but, in order to achieve a reduction of the concentration of acetylene to below said specified level, the temperature at which the product from the first bed is fed to the second bed is increased as the activity of the catalyst declines so that after a period of use the product from the first bed is heated before it is fed to the second bed.

It will be appreciated that in some cases it may be desirable to increase the first bed inlet temperature to some extent as the catalyst activity declines. However such an increase should be kept to a minimum so that, at least towards the end-of-life, heating of the product from the first bed, rather than cooling thereof, is necessary to achieve the desired second bed inlet temperature.

Where at least three beds are employed and the product from the second, and any succeeding, bed may be cooled before it is fed to a further bed. Alternatively it may be desirable in some cases to provide for heating of the product from the second and/or subsequent beds.

It will be appreciated that the changes in temperature may be effected stepwise or continuously.

It may also be desirable to provide bypass means whereby at least one of the beds is bypassed when the catalyst is fresh and only brought into use as the activity of the catalyst in at least one other bed declines.

In addition to hydrogenation of acetylene (ethyne), if other highly unsaturated compounds, eg methyl acetylene, propadiene, and butadiene, are present, some hydrogenation thereof may also occur.

The invention is illustrated by the following calculated examples based upon measured "start-", "middle-", and "end-of-life" catalyst activities.

EXAMPLE 1

In this example a system using three adiabatic beds is employed with each bed containing 20 m³ of a selective acetylene hydrogenation catalyst containing 0.04% by weight of palladium on a support of calcium aluminate; the feed gas of the following composition is fed at a rate of 11000 kmol/h to the first bed:

| Feed gas composition (volume %) | | | |
|---|---|---|---|
| hydrogen | 19.43 | propane | 10.00 |
| methane | 25.00 | propene | 10.00 |
| ethane | 5.00 | methyl acetylene | 0.05 |
| ethene | 30.00 | propadiene | 0.10 |
| ethyne | 0.35 | butadiene | 0.02 |
| carbon monoxide | 0.05 | | |

Comparison A

With a conventional system with inter-bed cooling, typical "start-of-life", "middle-of-life" and "end-of-life" conditions to achieve a product with an acetylene (ethyne) content of below 0.15 ppm by volume, the ethyne contents at the exit of each bed, and the ethene gain (defined as the increase in ethene resulting from hydrogenation of the acetylene less the loss of ethene resulting from hydrogenation of ethene, expressed as a percentage, by volume, of the ethene in the feed to the first bed) are shown in the following table.

| | $T_{in}$ (°C) | $T_{out}$ (°C) | ethyne (vppm) | ethene gain (% v) |
|---|---|---|---|---|
| Start-of-life | | | | |
| Bed 1 | 62 | 77 | 151.2 | |
| Bed 2 | 62 | 66 | 4.5 | |
| Bed 3 | 62 | 65 | 0.1 | 0.31 |
| Middle-of-life | | | | |
| Bed 1 | 72 | 85 | 870.7 | |
| Bed 2 | 72 | 81 | 8.9 | |
| Bed 3 | 72 | 77 | 0.1 | −0.24 |
| End-of-life | | | | |
| Bed 1 | 87 | 100 | 1696.3 | |
| Bed 2 | 87 | 103 | 9.9 | |
| Bed 3 | 87 | 95 | 0.1 | −1.51 |

Comparison B

Computer modelled studies show that optimum conditions with a three bed system having inlet temperatures within the range 50° C. to 90° C. and inter-bed cooling so that the second and third bed inlet temperatures are below the exit temperatures of the preceding bed are as shown in the following table.

| | $T_{in}$ (°C) | $T_{out}$ (°C) | ethyne (vppm) | ethene gain (% v) |
|---|---|---|---|---|
| Start-of-life | | | | |
| Bed 1 | 60 | 74 | 388.8 | |
| Bed 2 | 69 | 76 | 0.9 | |
| Bed 3 | 55 | 57 | 0.1 | 0.34 |
| Middle-of-life | | | | |
| Bed 1 | 69 | 80 | 1329.5 | |
| Bed 2 | 79 | 92 | 0.6 | |
| Bed 3 | 57 | 59 | 0.1 | −0.06 |
| End-of-life | | | | |
| Bed 1 | 78 | 85 | 2486.5 | |
| Bed 2 | 84 | 101 | 303 | |
| Bed 3 | 90 | 100 | 0.1 | −1.13 |

Invention

In this case the inlet temperature to bed 1 is kept low and the product from bed 1 is heated before entering bed 2. Computer modelled optimum "start-of-life", "middle-of-life" and "end-of-life" conditions in accordance with the invention are as shown in the following table assuming the conditions were otherwise as quoted above.

|  | $T_{in}$ (° C) | $T_{out}$ (° C.) | ethyne (vppm) | ethene gain (% v) |
|---|---|---|---|---|
| Start-of-life |  |  |  |  |
| Bed 1 | 50 | 55 | 2328.1 |  |
| Bed 2 | 71 | 86 | 0.4 |  |
| Bed 3 | 50 | 51 | 0.1 | 0.46 |
| Middle-of-life |  |  |  |  |
| Bed 1 | 50 | 52 | 3147.3 |  |
| Bed 2 | 79 | 100 | 0.2 |  |
| Bed 3 | 50 | 51 | 0.1 | 0.19 |
| End-of-life |  |  |  |  |
| Bed 1 | 50 | 51 | 3415.0 |  |
| Bed 2 | 90 | 115 | 1.8 |  |
| Bed 3 | 76 | 82 | 0.1 | −0.72 |

It is seen that, compared to the aforesaid comparisons A and B, there is a significant benefit in ethene gain throughout the catalyst life.

EXAMPLE 2

In a similar example but wherein the feed contained 0.5% by volume of a 0.35% by volume and correspondingly 4.85% ethane instead of 5%, the "end-of-life" data for the two comparisons and the invention are shown in the following table.

|  | $T_{in}$ (° C) | $T_{out}$ (° C.) | ethyne (vppm) | ethene gain (% v) |
|---|---|---|---|---|
| Comparison A |  |  |  |  |
| Bed 1 | 87 | 101 | 2665.4 |  |
| Bed 2 | 87 | 107 | 10.3 |  |
| Bed 3 | 87 | 95 | 0.1 | −0.96 |
| Comparison B |  |  |  |  |
| Bed 1 | 78 | 85 | 3796.0 |  |
| Bed 2 | 84 | 107 | 30.6 |  |
| Bed 3 | 90 | 100 | 0.1 | −0.6 |
| Invention |  |  |  |  |
| Bed 1 | 50 | 51 | 4906.6 |  |
| Bed 2 | 90 | 121 | 0.5 |  |
| Bed 3 | 63 | 66 | 0.1 | −0.06 |

In both Examples 1 and 2, some hydrogenation of the other highly unsaturated compounds present, ie propadiene, methyl acetylene and butadiene, takes place. It is calculated that in each of the comparisons and the process in accordance with the invention set out in Examples 1 and 2, the methyl acetylene content is reduced from 500 ppm to 70–100 ppm, the propadiene content from 1000 ppm to 750–790 ppm, and the butadiene content from 200 ppm to about 30–40 ppm, all expressed by volume.

We claim:

1. A process for the selective hydrogenation of acetylene in the presence of olefins to decrease the concentration of acetylene to below a specified level, comprising passing a hydrocarbon feedstock containing olefins and acetylene, together with hydrogen, through a first bed of a series of beds each containing a selective hydrogenation catalyst whose activity declines over a period of use, and passing the product from the first bed through the second bed of the series of beds, with the product from the first bed being heated before it is fed to the second bed, and, in order to achieve a reduction of the concentration of acetylene to below said specified level, the temperature at which the product from the first bed is fed to the second bed is increased as the activity of the catalyst declines.

2. A process according to claim 1 wherein the temperature at which the feedstock is fed to the first bed is increased as the catalyst activity declines.

3. A process according to claim 1 wherein at least three beds are employed and the product from the second, and any succeeding, bed is cooled before it is fed to a further bed.

4. A process for the selective hydrogenation of acetylene in the presence of olefins to decrease the concentration of acetylene to below a specified level, comprising passing a hydrocarbon feedstock containing olefins and acetylene, together with hydrogen, through a first bed of a series of beds each containing a selective hydrogenation catalyst whose activity declines over a period of use, and passing the product from the first bed through the second bed of the series of beds with the product from the first bed being cooled before it is fed to the second bed when the catalyst is fresh, but, in order to achieve a reduction of the concentration of acetylene to below said specified level, the temperature at which the product from the first bed is fed to the second bed is increased as the activity of the catalyst declines, so that after a period of use the product from the first bed is heated before it is fed to the second bed.

5. A process according to claim 4 wherein the temperature at which the feedstock is fed to the first bed is increased as the catalyst activity declines.

6. A process according to claim 4 wherein at least three beds are employed and the product from the second, and any succeeding, bed is cooled before it is fed to a further bed.

* * * * *